(12) United States Patent
Muriaux et al.

(10) Patent No.: US 8,969,305 B2
(45) Date of Patent: Mar. 3, 2015

(54) AQUEOUS OPHTHALMIC SOLUTION BASED ON CYCLOSPORIN

(71) Applicant: Laboratoires Thea, Clermont Ferrand (FR)

(72) Inventors: Emmanuel Muriaux, Maule (FR); Fabrice Mercier, Clermont-Ferrand (FR)

(73) Assignee: Laboratories Thea, Clermont Ferrand (FR)

( * ) Notice: Subject to any disclaimer, the term of this patent is extended or adjusted under 35 U.S.C. 154(b) by 0 days.

(21) Appl. No.: 13/796,392

(22) Filed: Mar. 12, 2013

(65) Prior Publication Data

US 2013/0267472 A1  Oct. 10, 2013

Related U.S. Application Data

(60) Provisional application No. 61/614,218, filed on Mar. 22, 2012.

(30) Foreign Application Priority Data

Mar. 22, 2012  (FR) ..................... 12 52583

(51) Int. Cl.
    *A61K 38/13*     (2006.01)
    *A61K 47/14*     (2006.01)
    *A61K 47/32*     (2006.01)
    *A61K 47/38*     (2006.01)
    *A61K 9/08*     (2006.01)
    *A61K 9/00*     (2006.01)

(52) U.S. Cl.
    CPC ................. *A61K 47/38* (2013.01); *A61K 38/13* (2013.01); *A61K 9/0048* (2013.01); *A61K 47/14* (2013.01); *A61K 47/32* (2013.01); *A61K 9/08* (2013.01)
    USPC ...................................... 514/20.5

(58) Field of Classification Search
    CPC ....... A61K 38/13; A61K 47/14; A61K 47/32; A61K 47/38; A61K 9/0048; A61K 9/08
    USPC ...................................... 514/20.5
See application file for complete search history.

(56) References Cited

U.S. PATENT DOCUMENTS

| | | |
|---|---|---|
| 6,677,304 B2 | 1/2004 | Di Napoli |
| 6,953,776 B2 | 10/2005 | Di Napoli |
| 2002/0173516 A1 | 11/2002 | Chen et al. |
| 2008/0039378 A1* | 2/2008 | Graham et al. ................. 514/11 |

FOREIGN PATENT DOCUMENTS

| | | |
|---|---|---|
| EP | 1 142 566 A1 | 10/2001 |
| WO | WO 93/23010 A1 | 11/1993 |
| WO | WO 2009/046967 A1 | 4/2009 |
| WO | WO 2009/058585 A2 | 5/2009 |
| WO | WO 2009/088570 A1 | 7/2009 |
| WO | WO 2009/099467 A2 | 8/2009 |

OTHER PUBLICATIONS

Definition of derivative from http://cancerweb.ncl.ac.uk/omd/about.html, pp. 1-5, accessed Jul. 7, 2005.*
Craik DJ, Daly NL, Saska I, Trabi M, Rosengren KJ, "Structures of naturally occurring circular proteins from bacteria," Jounral of Baceriology, Jul. 2003, 4011-4021.*
Hydroxymethyl cellulose from www.famtreemed.com/devitarx_line.html, pp. 1-4. Accessed Apr. 20, 2014.*
Hydroxyethyl celluose from www.simply-eden.com/pages/hydroxethyl-cellulose, p. 1. Accessed Apr. 20, 2014.*
Naturally occurring preservatives from www.cosmeticbusiness.com/technical/article_page/Natural_antimicrobial-and pre . . . , pp. 1-7. Accessed Apr. 20, 2014.*
Macrogolglycerol hydroxystearate 40 is castor oil from www.medicines.org.uk/emcmobile/medicine/27436/spc, pp. 1-11. Accessed Apr. 20, 2014.*
Castor oil is naturally occurring from altmedicine.about.com/od/constipation/a/Castor-Oil.htm, pp. 1-3. Accessed Apr. 20, 2014.*
Search Report for FR 1252583, mailed Oct. 31, 2012.
Lallemand et al., Cyclosporine A delivery to the eye: a pharmaceutical challenge. Eur J Pharm Biopharm. Nov. 2003;56(3):307-18.

* cited by examiner

*Primary Examiner* — Julie Ha
(74) *Attorney, Agent, or Firm* — Wolf, Greenfield & Sacks, P.C.; C. Hunter Baker; Wei Zhang

(57) ABSTRACT

Described herein is an aqueous ophthalmic solution containing an immunosuppressive agent, such as cyclosporin A, and at least three polymers. The three polymers are preferably a combination of a cellulose derivative, a polyvinyl derivative, and a macrogolglycerol hydroxystearate.

28 Claims, 2 Drawing Sheets

AQUEOUS OPHTHALMIC SOLUTION BASED ON CYCLOSPORIN

RELATED APPLICATIONS

The present application claims priority under 35 U.S.C. §119(e) to U.S. provisional application, U.S. Ser. No. 61/614,218, filed Mar. 22, 2012, and claims priority under 35 U.S.C. §119(a) to French application No. 1252583, filed Mar. 22, 2012, each of which is incorporated herein by reference

FIELD OF THE INVENTION

This invention proposes an aqueous ophthalmic solution containing an immunosuppressive agent such as cyclosporin A as the active ingredient. The said solution has toxicological and allergenic characteristics which are acceptable for treatment of eye surface disorders which have an immunological and/or inflammatory basis, such as dryness of the eye or loss of corneal sensitivity.

More precisely, the invention concerns an aqueous ophthalmic solution in which the active ingredient, in particular cyclosporin A, is formulated with a ternary polymeric system so that it can be solubilised in a therapeutically effective quantity and with good stability, even without any preservative.

STATE OF THE ART

Dry eye syndrome, also called ocular dryness or keratoconjunctivitis sicca (KCS), is a condition in which the lachrymal glands do not produce enough tears. It results in eye discomfort accompanied by itching, smarting and/or burning sensations.

Ocular dryness can result from an abnormality of the lachrymal glands, inflammation of the eyelids, eye inflammation due to an allergy, refractive surgery (particularly using lasers), deficiency in certain lipids in the daily diet, prolonged wearing of contact lenses, hormonal changes, an autoimmune disease, or side effects of certain medicinal products.

Loss of corneal sensitivity may, for example, result from the sequelae of surgery, ulceration or a viral infection (viral keratitis) of the cornea.

In the treatment of ocular dryness, the application of artificial tears, also known as lubricating or moistening eye drops, provides short-term local relief but does not solve the problem from a systemic point of view: they do not help the subject to improve the quantity or quality of the tears and are only a temporary substitution solution. Low or medium viscosity artificial tears are generally based on polyvinyl alcohols or cellulose derivatives, while those with higher viscosity contain carbomers or hyaluronic acid.

A more promising treatment for these two types of conditions is based on the topical application of cyclosporin A.

Cyclosporin A, generally called cyclosporin, is an effective immunosuppressive agent, particularly used in organ transplantation and to prevent the acute rejection of allografts.

It is thought that cyclosporin acts by inhibiting calcineurin, a phosphatase involved in the transcription of the interleukin 2 gene, normally secreted by T-lymphocytes. In addition, cyclosporin A inhibits the production of lymphokines and the release of interleukins, which lead to a substantial reduction in the activity of effector T-lymphocytes. In other words, cyclosporin A is a molecule which can inhibit or prevent the activity of the immune system.

Cyclosporin A is a cyclic peptide of eleven amino acids, synthesised by a microscopic fungus *Tolypocladium inflatum*. Cyclosporin A has the formula [R-[[R*,R*-(E)]]-cyclic(L-alanyl-D-alanyl-N-methyl-L-leucyl-N-methyl-L-leucyl-N-methyl-L-valyl-3-hydroxy-N,4-dimethyl-L-2-amino-6-octenoyl-L-α-amino-butyryl-N-methylglycyl-N-methyl-L-leucyl-L-valyl-N-methyl-L-leucyl) (CAS number 59865-13-3), with the following structure:

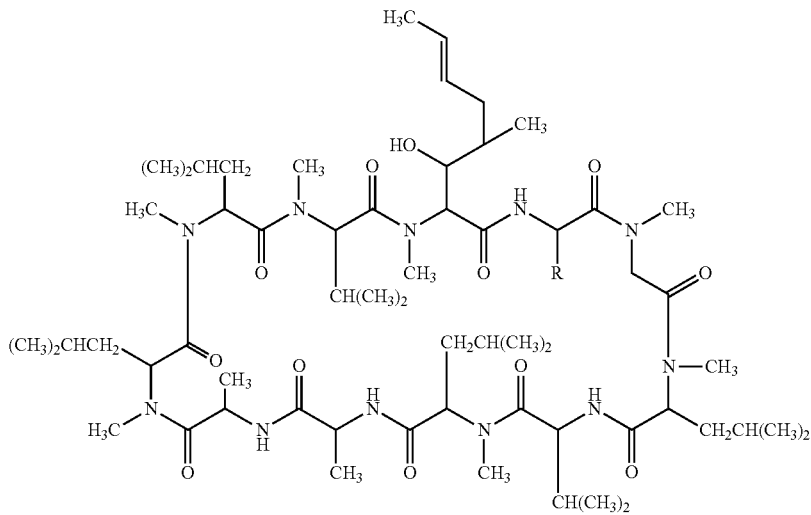

CYCLOSPORINE

A practical difficulty with cyclosporin A is that it is only very slightly soluble in aqueous media, in the order of 20-30 µg/l at 25° C., i.e., 0.002 to 0.003% by weight (w/v). On the other hand, this molecule is soluble in alcohols (e.g., ethanol or methanol), acetonitrile, ethyl acetate and oils (e.g., olive oil, maize oil or castor oil).

This same problem of solubility occurs with other ophthalmic immunosuppressive agents such as tacrolimus (CAS number: 104987-11-3) or rapamycin (CAS number: 53123-88-9).

Considerable efforts have been made to obtain an eyewash formulation, for ocular treatment of dry eyes and loss of sensitivity of the cornea, with acceptable tolerance to instillation and bioavailability of cyclosporin A in the target tissues.

Tolerance is measured by the irritation caused by the eyewash in the eye following its instillation, e.g., by using the scale produced by Draize et al. (Methods for the study of irritation and toxicity of substances applied topically to the skin and mucous membranes. *J. Pharmacol. and Exp. Therapeutics*, 1944; 82: 377-390).

Moreover, the efficacy of eyewash penetration reflects the bioavailability of cyclosporin A in the various tissues encountered after instillation, i.e., the conjunctiva (bulbar and palpebral) and the cornea.

Given the very low solubility of cyclosporin A in water, developments in the ophthalmic area have focused on eyewashes in the form of emulsions or hydro-alcoholic solutions.

Thus, cyclosporin A is commercially available in the United States in the form of a 0.05% emulsion in castor oil. This product, sold in preservative-free single doses under the name of RESTASIS™ (ophthalmic emulsion containing cyclosporine (0.05%), glycerin, castor oil, polysorbate 80, carbomer copolymer type A, purified water, and sodium hydroxide), is recommended for the treatment of keratoconjunctivitis sicca.

In Europe, and more particularly in France, the administration of cyclosporin A relies essentially on hospital preparations. However, these hospital preparations, in which the concentration varies between 0.05 and 2% as an active formula in an oily medium (olive oil, castor oil or maize oil) and/or in the presence of alcohol, are only stable for a few weeks.

Moreover and in both cases, the tolerance to instillation is not good, which detracts from good compliance with the treatment, and thus its efficacy.

Nourry et al. (Etude de la cytotoxicité de différents collyres à base de ciclosporine A buvable (SANDIMMUN™ (concentrate for intravenous infusion containing cyclosporine, polyoxyethylated castor oil, macrogolglycerol ricinoleate, and ethanol; or oral solution containing cyclosporine, maize oil, ethanol, and inter-esterified maize oil)). *J. Fr. Ophtalmol.*, 2006; 29, 3, 251-257) suggested that the excipients (oil and/or alcohol) of these eyewashes cause side effects, such as irritation of the conjunctiva or hyperaemia, toxicity of the corneal epithelium, itching, or burning sensations. The same authors compared the tolerance of hydro-alcoholic and oily (emulsion) eyewashes and concluded that oily eyewashes are less irritant on instillation than hydro-alcoholic eyewashes.

This is the reason why the most recent developments in eyewashes based particularly on cyclosporin A aim to improve the efficacy of oily or emulsion eyewashes, in order to increase their tolerance on instillation while at the same time overcoming the problems of solubility.

There is nevertheless a need to develop immunosuppressant-containing ophthalmic formulations, in particular containing cyclosporin A, with the following characteristics:
  Presented in the form of aqueous solutions,
  Stable over time,
  Well tolerated by the eye following instillation,
  Good penetration of the cornea, and
  Containing a suitable dose for treating, in particular, dry eye syndrome and the loss of corneal sensitivity.

DESCRIPTION OF THE INVENTION

In this invention, despite the low solubility of immunosuppressants, the inventors have developed a stable aqueous solution, possibly preservative-free, in which the concentration of cyclosporin A ensures that the product is effective and the pharmaceutical formulation guarantees very good tolerance on instillation.

According therefore to a first embodiment, this invention concerns an aqueous ophthalmic solution containing an immunosuppressive agent, preferably cyclosporin A, and at least three polymers.

Due to the combined use of three judiciously chosen polymers, an effective therapeutic quantity of the immunosuppressant, preferably cyclosporin A, can be dissolved in water while the said composition is provided with suitable viscosity for topical ocular application. In other words the three polymers play a role in the solubilisation and/or gelification and are defined as solubilising agents and/or gelling agents, even co-solubilising and/or co-gelling agents.

The aqueous ophthalmic solution according to the invention thus includes, as its active substance, a slightly soluble immunosuppressive agent, preferably cyclosporin A. Nevertheless it is possible to apply the same formulation principle to other topical ocular immunosuppressive agents which are only slightly soluble in water, such as other forms of cyclosporin, tacrolimus (CAS number: 104987-11-3) or rapamycin (CAS number: 53123-88-9).

The concentration of active substance in the solution, particularly cyclosporin A, is appropriately between approximately 0.01 and approximately 0.2% by weight of the solution (weight/volume or w/v), preferably between approximately 0.05 and approximately 0.1%. These are effective therapeutic quantities, and they are compatible with the solubilisation limits of the proposed formulation system. According to a certain embodiment, particularly for cyclosporin, the concentration is greater than or equal to approximately 0.05% by weight, preferably greater than approximately 0.05%, more preferably greater than or equal to approximately 0.1% by weight, which corresponds to a solubilized quantity never reached in the context of an aqueous solution. For immunosuppressive agents other than cyclosporin, especially for those having a greater solubility in water, the weight/volume ratio in the solution according to the invention can be greater than or equal to approximately 0.1%, preferably greater than or equal to approximately 0.2%, more preferably greater than or equal to approximately 0.5% or even approximately 1%.

It should be noted that a solution according to the invention can also comprise other active substances from the same category (i.e., immunosuppressive agents) or from another category. In an adapted manner, said other active substance(s) is (are) also in a solubilized form. According to a certain embodiment, the other active substance(s) is (are) not a corticosteroid.

The composition according to the invention is characteristically presented as an aqueous solution. By definition, an aqueous solution is a liquid phase containing several chemical species, of which one, i.e., water ($H_2O$), is the major species and acts as solvent (or vehicle) for the minor species forming the solutes or "dissolved chemical species". Advantageously, the solution according to the invention contains no organic solvent, particularly no alcohol such as ethanol.

In the invention, cyclosporin is dissolved in the solution, and not as micelles or in an emulsion (in an oily phase) as in the prior art. Preferably, the solution according to the invention therefore contains no oil, particularly none of plant origin such as castor oil.

According to another embodiment, the solution according to the invention is essentially free of particles, especially as defined by the method 2.9.19 in the European Pharmacopoeia. In particular, the solution is advantageously free of micelles.

According to the invention, this solubilisation is provided by a ternary polymer system:

The aqueous ophthalmic solution according to the invention contains a first polymer, preferably selected from cellulose derivatives, more precisely from cellulose ethers. Surprisingly, while these derivatives are known for their gelling properties, the inventors have observed that they allow pre-solubilisation of the immunosuppressant, preferably cyclosporin A. This first polymer can therefore be defined as a co-solubiliser/co-gelling agent.

Preferably, the cellulose derivative is chosen from the group including: methylcellulose, ethylcellulose, hydroxyethylcellulose, hydroxypropylcellulose, carboxymethylcellulose, hydroxypropylmethylcellulose, and their salts. More preferably, it is sodium (Na) carboxymethylcellulose.

The concentration of this first polymer, preferably a cellulose derivative, is between appropriately 0.1 and appropriately 3% by weight of the solution (weight/volume or w/v), preferably between appropriately 0.5 and appropriately 1.5%, and more preferably equal to appropriately 0.8%.

According to a particular embodiment, the immunosuppressive agent, preferably cyclosporin A, is pre-solubilised in a first step in the presence of this first polymer in water. This first step results in a suspension, which is then mixed with the other two polymers of the solution.

The aqueous ophthalmic solution according to the invention includes a second polymer, preferably a polyvinyl polymer, more preferably polyvinyl alcohol.

Polyvinyl alcohol (CAS number 9002-89-5) is known for its gelling properties, hence its use as a gelling agent. Remarkably, this polyvinyl derivative participates notably in the co-solubilisation of cyclosporin A, potentially through the use of its hydroxyl groups.

Another polyvinyl derivative which can be used is polyvinyl pyrrolidone or povidone (PVP) (CAS number 9003-39-8).

The concentration of the second polymer, preferably a polyvinyl derivative, is between appropriately 0.25 and appropriately 3% by weight of the solution (weight/volume or w/v), preferably equal to appropriately 0.5%.

These 2 polymer categories are selected notably from the family of excipients widely used for the formulation of eyewashes intended for the treatment of ocular dryness. Thus, whereas for treatment with RESTASIS™ (ophthalmic emulsion containing cyclosporine (0.05%), glycerin, castor oil, polysorbate 80, carbomer copolymer type A, purified water, and sodium hydroxide), concomitant application of artificial tears is recommended, the ophthalmic solution according to the invention acts as a "2 in 1" product.

The aqueous ophthalmic solution according to the invention characteristically includes a third polymer, playing the role of a solubilising agent, preferably a non-ionic polymer. Preferably it is a polymer with a lipophilic functional group, such as macrogolglycerol hydroxystearate. Macrogolglycerol hydroxystearate is a non-ionic solubilising agent, suitable for co-solubilising, for example, cyclosporin A, particularly because of its apolar part.

These polymers are composed of a fatty acid molecule (in C18, omega-9 hydroxylated, ricinoleic acid or (R)-(+)-12-hydroxy-9Z-octadecenoic acid (apolar part) and 35 molecules of polyethylene glycol H—(O—CH=CH)$_n$—OH, with varying lengths of carbon chain ($C_7$, $C_{25}$, $C_{40}$ or $C_{60}$) defining the grades 7, 25, 40 or 60.

Still more preferably, the third polymer is macrogolglycerol hydroxystearate 40, also called PEG 40 hydrogenated castor oil, its CAS number being 61788-85-0.

The concentration of the third polymer, preferably macrogolglycerol hydroxystearate, is between appropriately 0.5 and appropriately 20% by weight of the solution (weight/volume or w/v), preferably between appropriately 5 and appropriately 15%, and more preferably equal to appropriately 10%. It is thus the major polymer of the ternary system.

Preferably, the solution according to the invention contains no cyclodextrin. According to another embodiment, it contains no penetration enhancer such as BAK (benzalkonium chloride) or DMSO, known to help the solubilisation of active substances and to destabilize the membrane of the cells constituting the corneal epithelium.

Preferably, combining these three polymers provides the solution according to the invention with viscosity suitable for the required topical ophthalmic application.

Thus, the appropriate viscosity of the solution according to the invention is lower than or equal to appropriately 50 mPa·s (cP), preferably between appropriately 5 and appropriately 50 mPa·s, and more preferably between appropriately 5 and appropriately 15 mPa·s, when measured using a Brookfield RVDV III rotational viscometer at 25° C.

In practice, this viscosity is preferably close to the viscosity of human tears, evaluated at approximately 6.5 mPa·s at 20° C. and with a velocity gradient close to zero. Application of the solution according to the invention thus causes no sensation of discomfort or irritation. Indeed, it has been determined that easy elimination with no discomfort is only possible if the viscosity of the ophthalmic solution/tears mixture is lower than appropriately 50 mPa·s.

The aqueous ophthalmic solution naturally may, in addition, contain an additive selected from the group of non-ionic isotonifying agents, antioxidant agents and/or buffer systems.

The solution according to the invention preferably has a neutral pH, preferably between 6.5 and 7. Preferably, it is an isotonic formulation, with osmolality preferably between 290 and 350 mosmol/kg.

In a particular embodiment, the solution according to the invention is composed of the ingredients listed in the table below, preferably according to the centesimal formula shown:

| PRODUCT | FUNCTION | CENTESIMAL FORMULA (g/100 g) |
|---|---|---|
| Cyclosporin A | Active product | 0.01 to 0.10 g |
| Macrogolglycerol hydroxystearate 40 | Co-solubilising agent/Co-gelling agent | 10.0 g |
| Sodium carboxymethylcellulose | Co-solubilising agent/Co-gelling agent | 0.80 g |
| $NaH_2PO_4 \cdot H_2O$ | Buffer | 0.520 g |
| $Na_2HPO_4 \cdot 2H_2O$ | Buffer | 0.652 g |
| PVA | Co-solubilising agent/Co-gelling agent | 0.50 g |
| Water | — | qs 100 g |

As indicated in the application and preferably, the solution according to the invention is free of antimicrobial preservatives, especially free of ammonium quaternary type of preservative such as for example benzalkonium chloride (BAK).

In this invention, "antimicrobial preservative" or "antimicrobial" means a preservative agent with antimicrobial properties, i.e., a compound capable of guaranteeing the protection of the ophthalmic solution from possible microbial contamination. Compounds of the ammonium quaternary type, particularly benzalkonium chloride (BAK) or polyquad, possibly associated with EDTA (e.g., disodium edetate), are usually used as preservatives.

Other possible preservatives include but are not limited to:
Guanidine-based preservatives, such as PHMB or chlorhexidine;
Benzyl alcohol;
Parabens, such as methylparaben or propylparaben;
Mercury-based preservatives, such as Thimerosal;
Chlorbutanol;
Benzethonium chlorides;
Oxidative-type preservatives such as Purite.

The invention's formulation can be supplied as single-use (unidose) or multi-dose vials such as ABAK® (preservative-free, multi-dose drop dispenser containing a 0.2 micron nylon fibre membrane), COMOD® (preservative-free, airless, multi-dose drop dispenser that dispenses one drop every time the dispenser is pressed) or equivalent, to allow the ophthalmic solution to be used without preservatives for several days.

The invention therefore also concerns a single-use (unidose) or multidose vial containing the ophthalmic solution previously described, e.g., made in LDPE, preferably, of additive-free quality according to European Pharmacopoeia.

In addition, the solution according to the invention is stable for at least 24 months, or for at least 36 months, at ambient temperature (25° C.-30° C.).

The invention also concerns the use of this solution in treating disorders of the surface of the eye which have an immunological and/or inflammatory basis.

The invention also provides methods of treating and preventing ophthalmic diseases, in particular, diseases with an immunological and/or inflammatory basis.

In human ophthalmology, this solution is particularly suited for treatment of dry eye syndrome and/or loss of corneal sensitivity.

Indications relating to loss of corneal sensitivity are, for example, related to:
an operation affecting the cornea;
a viral infection (e.g., herpes HSV-I, HSV-II or VZV viruses);
keratorefractive surgery or penetrating keratoplasty;
a radial keratotomy;
a photorefractive keratotomy;
a LASIK (laser-assisted in situ keratomileusis) operation, in particular EPI-LASIK (epithelial LASIK) or LASEK (laser sub-epithelial keratomileusis).

Moreover, a solution according to the invention can be used in veterinary medicine, particularly in the following cases:
Keratoconjunctivitis sicca in dogs;
Problems of corneal neovascularisation, corneal pigmentation and cellular infiltration in chronic superficial keratitis (CSK) in dogs, cats and horses;
Lymphoplasmocytic infiltration of the nictitating membrane in dogs;
Eosinophilic keratitis in cats and horses;
Punctate keratitis in dogs (Teckel, etc.) and horses;
Keratouveitis, endothelitis, certain torpid ulcers and periodic fluxion of horses;
In combination, in the treatment of inflammatory reactions of immune origin in dogs, cats and horses;
In the prevention of corneal graft rejection in dogs, cats and horses.

In practice, the solution according to the invention is administered to humans or non-human animals via the topical route, in the form of one or more drops per day in each eye.

In another embodiment and particularly relating to the use of a cellulose derivative as an excipient, the invention concerns a process for preparing the solution according to the invention, comprised of the following steps:
Presolubilising the immunomodulator agent, preferably cyclosporin A, in the presence of at least a fraction of the first polymer (preferably appropriately 25% by weight), preferably a cellulose derivative, in the presence of water and preferably while stirring;
Mixing the remaining fraction if any of the first polymer (preferably appropriately 75% by weight), preferably a cellulose derivative, with the two other polymers, water and possibly the buffer systems and isotonifying agents, preferably while stirring and/or heating, e.g., to a temperature of 60° C.;
Mixing the products obtained in the previous steps, preferably while stirring and/or heating, e.g., to a temperature of 60° C.

At the end of said process, in view of its conservation and its use in ophthalmology, said solution can be sterilized by heat, preferably by autoclave.

As is evident from the application, the aqueous ophthalmic solution according to the invention has several original features and advantages:
It is stable over time;
It is better tolerated by instillation than an oily emulsion and/or a hydro-alcoholic solution;
It penetrates the cornea well, without accumulating in the conjunctiva or passing into the aqueous humor or into the blood;
It contains a dose of cyclosporin A suitable for treating ocular surface disorders with an immunological and/or inflammatory basis, such as ocular dryness and/or the loss of corneal sensitivity.

EXAMPLES OF EMBODIMENTS

The invention and the advantages ensuing from it are better illustrated by the following non-exhaustive examples, given for informational purposes only, supported by the attached figures, in which.

I—PREPARATION OF A SOLUTION OF 0.1% (W/W) CYCLOSPORIN A (100 KG BATCH)

Figure 1A:
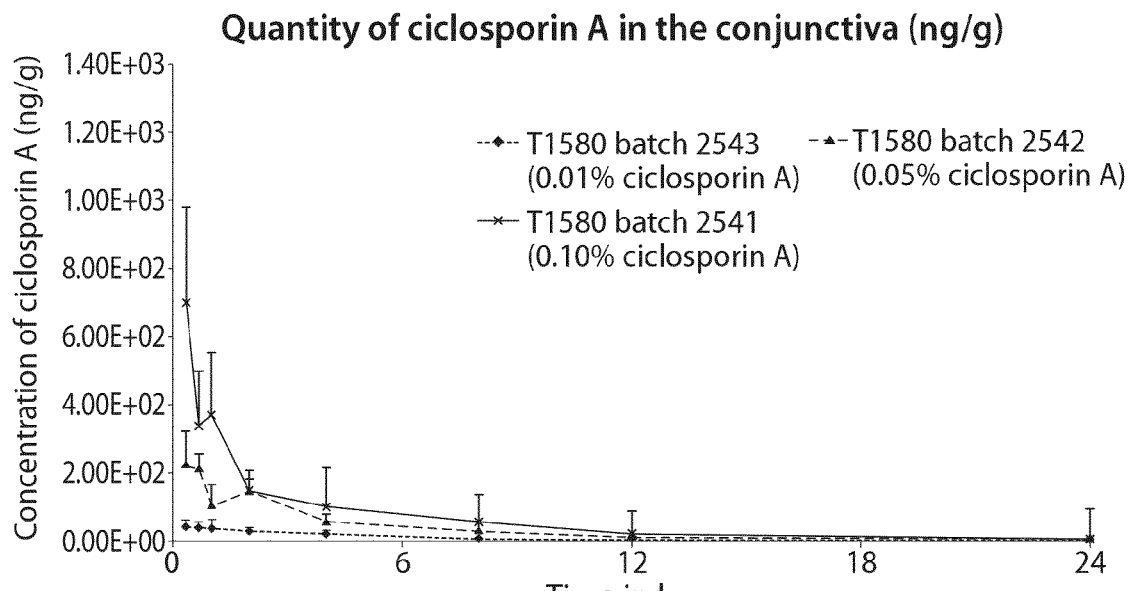
FIG. 1 illustrates ocular penetration over time, in the conjunctiva (A) and cornea (B), of cyclosporin A at three concentrations (0.01, 0.05 and 0.1% respectively).

I-1/Preparation of Fraction A:
200 g of sodium carboxymethylcellulose powder (the first polymer; 25% of the final quantity) are mixed with 100 g of cyclosporin A powder (the active substance, of a quality complying with the European Pharmacopoeia monograph) then 3 liters of water are added. This is mixed by stirring for an hour.

Cyclosporin A is in the form of a fine powder, which is toxic for the operator. This first pre-solubilisation step produces a milky suspension of cyclosporin A, which is much safer for the operator.

I-2/Preparation of Fraction B:
500 g of polyvinyl alcohol (or PVA, the second polymer) are added to approximately 65 liters of cold water (75% of the final volume of water). This is mixed while stirring, gradually increasing the temperature to 60° C.

When the PVA has dissolved (after a minimum of 30 minutes at 300 rpm), 10 kg of macrogolglycerol hydroxystearate 40 (or PEG 40 hydrogenated castor oil, the third polymer) are added. The solution is mixed while stirring for approximately 20 minutes at 60° C.

The buffers ($NaH_2PO_4 \cdot H_2O$ and $Na_2HPO_4 \cdot 2H_2O$), are then incorporated and the solution is mixed while stirring for 20 minutes at 60° C. Under the same conditions (approximately 20 min at 60° C.), 600 g of sodium carboxymethylcellulose are subsequently added (the first polymer; 75% of the final quantity).

I:-3/Preparation of the Final Solution:

Fraction A is added to fraction B. Following homogenisation, the final volume is made up with water and mixed for 10 minutes at 60° C.

The aqueous ophthalmic solution thus obtained is sterilised at 121° C. for 20 minutes while stirring. It may be packaged without any preservative, particularly an antimicrobial preservative, either in single-use LDPE (low density polyethylene) vials or in multidose ABAK® (preservative-free, multidose drop dispenser containing a 0.2 micron nylon fibre membrane) or COMOD® (preservative-free, airless, multidose drop dispenser that dispenses one drop every time the dispenser is pressed) vials or another type.

It should be noted that the preparation time of the sterile aqueous ophthalmic solution according to the invention is markedly shortened (maximum 8 hours) compared with prior art protocols, particularly published PCT application WO 2009/099467, in which at least one of the mixing steps occurs overnight.

This manufacturing process allows a conventional approach for the industrial production of sterile ophthalmic products, without prolonged stoppage of the industrial equipment, a risk factor in terms of microbial growth.

I-4/Composition of the Solution Obtained:

| PRODUCT | FUNCTION | CENTESIMAL FORMULA (g/100 g or %) |
|---|---|---|
| Cyclosporin A | Active substance | 0.10 |
| Macrogolglycerol hydroxystearate 40 | Solubilising agent | 10.0 |
| Sodium carboxymethylcellulose | Cosolubilising agent/gelling agent | 0.80 |
| $NaH_2PO_4 \cdot H_2O$ | Buffer | 0.520 |
| $Na_2HPO_4 \cdot 2H_2O$ | Buffer | 0.652 |
| PVA | Gelling agent | 0.50 |
| Water | Vehicle | qs 100 |

It should be noted that an identical protocol can be applied for the preparation of a solution with a cyclosporin A concentration between appropriately 0.01 and appropriately 0.1% (w/v), e.g., at appropriately 0.05%.

I-5/Characteristics of the Solution Obtained:

| Tests | Specifications |
|---|---|
| Appearance | Slightly opalescent, colourless solution |
| pH | 6.79 |
| Osmolality (mOsmol.kg) | 303 |
| Opalescence (NTU) | 3.65 |
| Coloration (method 2.2.2 Ph. Eur.: A solution is said to be colourless if it has the appearance of water or of the solvent, or if it is no more coloured than control solution $B_9$) | <B9 |
| Particles (method 2.9.19 Ph. Eur.) | Complies |
| Particles >= 10 μm | 570 (<6000) |
| Particles >= 25 μm | 17 (<600) |
| Viscosity (mPa.s) | 7.55 |
| Active substance concentration (g/100 ml) | 0.099 |

It is apparent that the solution obtained has the following advantages:

Neutral pH;

Isotonic formulation;

Viscosity close to that of human tears. Indeed, the viscosity in human tears at 20° C. would be approximately 6.5 mPa·s with a velocity gradient close to zero. The force exerted by the eyelids during normal blinking is approximately 0.2 N and during forced blinking approximately 0.7-0.8 N. In the presence of the solution according to the invention, the patient does not experience any uncomfortable sensation or irritation, which appears during blinking when the eyelids have to move a force greater than or equal to 0.9 N, since this sensation of discomfort is caused by reflex blinking to induce rapid elimination by means of tears.

This solution is a high tolerance formulation, obtained despite the very poor solubility of the active substance in water.

II—STABILITY OF THE SOLUTION ACCORDING TO THE INVENTION

Stability tests at 25° C. (Table 1) and 40° C. (Table 2) have demonstrated very good stability of the solution according to the invention, so that a shelf-life can be claimed of 36 months in storage conditions at ambient temperature.

TABLE 1

Stability of the aqueous ophthalmic solution according to the invention at 25° C. and 40% relative humidity

| TESTS | NORMS | Initial | 6 months | 12 months | 24 months | 36 months |
|---|---|---|---|---|---|---|
| Appearance | Viscous, opalescent, colourless to slightly yellow solution | Complies | Complies | Complies | Complies | Complies |
| pH | 6.5-7.0 | 6.79 | 6.72 | 6.70 | 6.71 | 6.58 |
| Osmolarity (mosmol/kg) | 290-350 | 303 | 300 | 303 | 296 | 301 |
| Opalescence (NTU) | <5.1 NTU (sol III Ph. Eur.) | 3.65 | 4.33 | 4.03 | 4.37 | 4.81 |
| Coloration | <B9 | <B9 | <B9 | <B9 | <B9 | <B9 |
| Particles | Absent | Absent | Absent | Absent | Absent | Absent |

TABLE 1-continued

Stability of the aqueous ophthalmic solution according to the invention at 25° C. and 40% relative humidity

| TESTS | NORMS | Initial | 6 months | 12 months | 24 months | 36 months |
|---|---|---|---|---|---|---|
| Viscosity (mPa · s) | >5 mPa · s | 7.55 | 7.55 | 7.51 | 7.17 | 7.25 |
| Cyclosporin A content | 0.090%-0.110% | 0.099 | 0.100 | 0.100 | 0.099 | 0.100 |
| Total impurities content | <2.5% | 1.15 | 1.22 | 1.03 | 0.92 | 1.14 |
| Sterility test | Complies | Complies | Complies | Complies | Complies | Complies |

TABLE 2

Stability of the aqueous ophthalmic solution according to the invention at 40° C. and 25% relative humidity

| TESTS | NORMS | Initial | 3 months | 6 months | 12 months |
|---|---|---|---|---|---|
| Appearance | Viscous, opalescent, colourless to slightly yellow solution | Complies | Complies | Complies | Complies |
| Osmolarity (mosmol/kg) | 290-350 | 303 | 304 | 311 | 318 |
| Opalescence (NTU) | <5.1 NTU (sol III Ph. Eur.) | 3.65 | 4.04 | 4.60 | 4.62 |
| Coloration | <B9 | <B9 | <B9 | <B9 | <B9 |
| Particles | Absent | Absent | Absent | Absent | Absent |
| Viscosity (mPa · s) | >5 mPa · s | 7.55 | 7.17 | 7.08 | 6.66 |
| Cyclosporin A content | 0.0900%-0.1100% | 0.0994 | 0.0991 | 0.0992 | 0.0981 |
| Total impurities content | <2.5% | 1.15 | 1.12 | 1.23 | 1.04 |

III—OCULAR TOLERANCE OF THE SOLUTION ACCORDING TO THE INVENTION

A solution of 0.1% by weight of cyclosporin A, prepared as described above, was tested in the rabbit, with 8 daily instillations of 50 µl for 7 days.

The following ocular examinations were made:
Observation of both eyes using an ophthalmoscope to assess them on the Draize scale, before treatment and following the last instillation of the day;
Ocular examinations of both eyes using a slit lamp to assess them using the McDonald-Shadduck scale, before treatment, on day 1 just before the last administration, then on day 8;
Collection and fixation of all the eyes.

Good ocular tolerance of the solution according to the invention was seen in the rabbit compared with other formulations, particularly compared with an alcoholic preparation with a non-ionic surface-active agent such as MODUSIK-A® (ophthalmic solution containing cyclosporin A (0.1%) and vehicle).

IV—KINETIC STUDY OF A SOLUTION ACCORDING TO THE INVENTION COMPARED WITH A COMMERCIAL EMULSION (RESTASIS™ (OPHTHALMIC EMULSION CONTAINING CYCLOSPORINE (0.05%), GLYCERIN, CASTOR OIL, POLYSORBATE 80, CARBOMER COPOLYMER TYPE A, PURIFIED WATER, AND SODIUM HYDROXIDE))

The ocular distribution of cyclosporin A was analysed on a pool of conjunctivas (bulbar and palpebral) and on the cornea, after a single instillation of 50 µl into the right eye of rabbits of:

an aqueous solution according to the invention, containing 0.05% (by weight) of cyclosporin A, prepared as described in point I and labelled T1580;

RESTASIS™ (ophthalmic emulsion containing cyclosporine (0.05%), glycerin, castor oil, polysorbate 80, carbomer copolymer type A, purified water, and sodium hydroxide), a commercial emulsion containing 0.05% (by weight) of cyclosporin A.

To do this, 48 pigmented rabbits (Fauve de Bourgogne—ref: HY R NZ 104) were divided into 2 groups of 24 animals. Each sub-group was then subdivided into 6 groups of 4 animals, corresponding to 6 analysis times (20 minutes, 40 minutes, 1 hour, 4 hours, 12 hours and 24 hours respectively). The animals received a single instillation of 50 µl of T1580 or RESTASIS™ (ophthalmic emulsion containing cyclosporine (0.05%), glycerin, castor oil, polysorbate 80, carbomer copolymer type A, purified water, and sodium hydroxide) into the right eye. At each analysis time the animals were sacrificed to obtain the samples of conjunctiva (bulbar and palpebral) (Cj) and cornea (Co), preserved at −20° C. until measurement. The cyclosporin A content was determined in the conjunctivas and corneas by HPLC-MS (high performance liquid chromatography combined with mass spectrometry).

The results are given in Table 3 below, in which:

$C_{max}$ is the maximum concentration observed;

$T_{max}$ is the time required to reach the maximum concentration; and

AUC is the area under the curve for the time between time zero and the time corresponding to the last measurable concentration. For this calculation, the random method for non-sequential samples is used.

TABLE 3

Pharmacokinetic comparison of the aqueous ophthalmic solution according to the
invention and the commercial emulsion RESTASIS ™ (ophthalmic
emulsion containing cyclosporine (0.05%), glycerin, castor oil, polysorbate 80,
carbomer copolymer type A, purified water, and sodium hydroxide),
each containing 0.05% of cyclosporin A.

|  | Cyclosporin A in the conjunctiva (Cj) | | | Cyclosporin A in the cornea (Co) | | |
| --- | --- | --- | --- | --- | --- | --- |
|  | $C_{max}$ (ng/g) | $T_{max}$ (h) | AUC | $C_{max}$ (ng/g) | $T_{max}$ (h) | AUC |
| T1580 | 453 | 0.33 | 966 | 769 | 0.66 | 8189 |
| RESTASIS ™ (ophthalmic emulsion containing cyclosporine (0.05%), glycerin castor oil, polysorbate 80, carbomer copolymer type A, purified water, and sodium hydroxide) | 257 | 0.33 | 924 | 504 | 1 | 6516 |

It can be seen that after an instillation of 50 μl of T1580 or RESTASIS™ (ophthalmic emulsion containing cyclosporine (0.05%), glycerin, castor oil, polysorbate 80, carbomer copolymer type A, purified water, and sodium hydroxide) into the right eye of pigmented rabbits, cyclosporin A is mainly found in the conjunctiva between 20 minutes and 4 hours, and in the cornea between 20 minutes and 24 hours later. The animals treated with T1580 had a larger quantity of cyclosporin A in the conjunctiva and the cornea between 20 minutes and 12 hours, in particular, in the cornea, compared with animals treated with RESTASIS™ (ophthalmic emulsion containing cyclosporine (0.05%), glycerin, castor oil, polysorbate 80, carbomer copolymer type A, purified water, and sodium hydroxide). This shows better availability of the active substance when formulated according to the invention.

V—PHARMACOKINETIC STUDY OF A SOLUTION ACCORDING TO THE INVENTION ADMINISTERED AS A SINGLE Dose at Three Different Concentrations The ocular penetration of a single dose of solution according to the invention was determined in the conjunctiva and the cornea following instillation of 25 μl into each eye of pigmented rabbits as a function of time (0.33, 0.66, 1, 2, 4, 8, 12 and 24 h after instillation). Three cyclosporin A concentrations were tested: 0.01, 0.05 and 0.1% w/w. The study was made on 72 rabbits, i.e., 3 rabbits per time period.

Figure 1B:
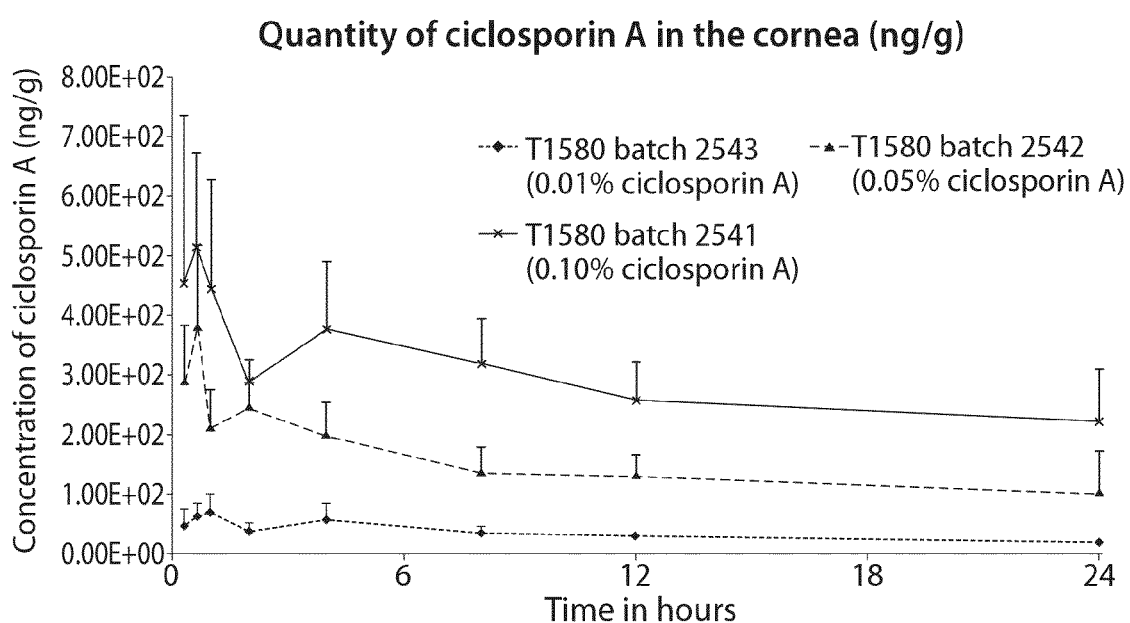

FIG. 1A, for the conjunctivas, and FIG. 1B, for the corneas, show a dose-dependent effect between the cyclosporin A concentration and the pharmacokinetic profile obtained for the conjunctivas and corneas.

The AUC obtained for the corneas is 4 to 5 times the size of that measured for the conjunctivas and the cyclosporin A remains longer in the corneas than in the conjunctivas, which demonstrates a particular tropism of cyclosporin A for the cornea.

VI—PHARMACOKINETIC STUDY OF A SOLUTION ACCORDING TO THE INVENTION ADMINISTERED AS REPEATED INSTILLATIONS

In this study, pigmented rabbits received an instillation in each eye (right and left eyes) of a dose (25 μl) of a solution according to the invention containing 0.1% (w/w) of cyclosporin A three times a day for 10 days.

More precisely, instillation was continued for 9 days (i.e., 27 instillations), then the pharmacokinetic profile was determined on the 28$^{th}$ instillation, i.e., on the morning of day 10 (D10). A sample was taken at time 0 (C0 trough estimation) then after 0.33 h and 0.66 h corresponding to Cmax for the conjunctivas and the cornea, then at 1, 2, 4, 8 and 24 hours.

Figure 2:
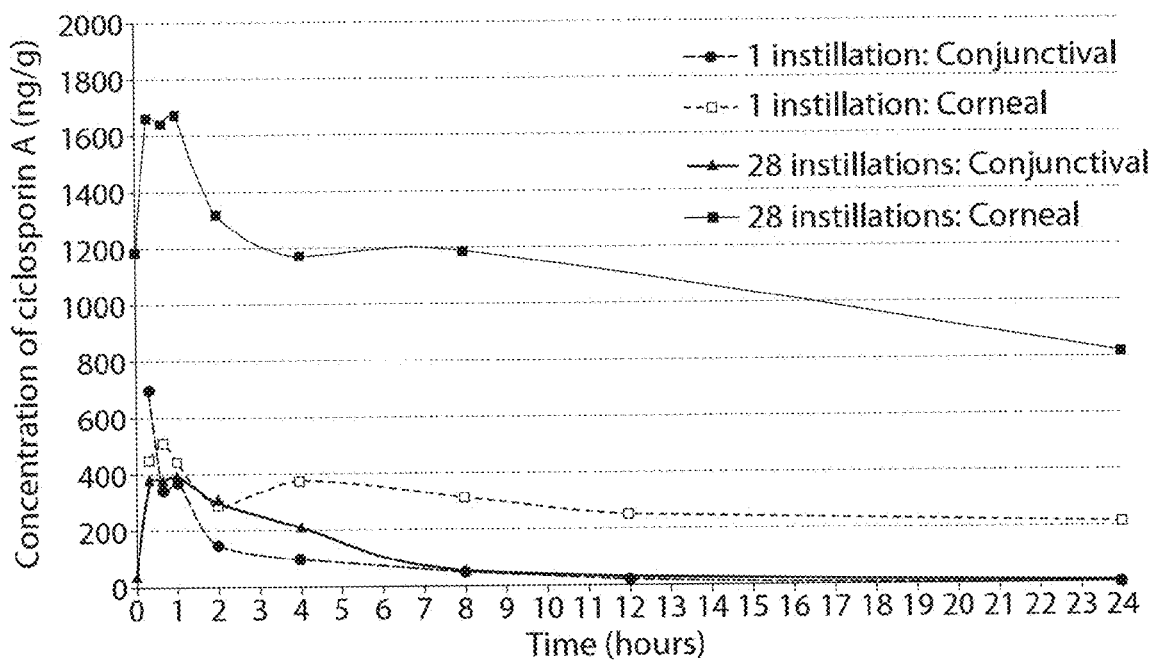
FIG. 2 illustrates the pharmacokinetic profile, in the conjunctiva (Cj) and cornea (Co), of a solution according to the invention containing 0.1% cyclosporin A, following repeated instillation (3 doses per day for 9 days (multi-dose), and analysis of the $28^{th}$ dose on D10).

The results are given in FIG. 2. At this concentration and dose:

There was no accumulation of cyclosporin A in the conjunctivas, nor did the concentration persist. In this structure, the nycthemeral immunomodulator cover over a 24-hour period seems to be limited in time;

Accumulation occurred in the cornea and a dose of 1,000 to 2,000 ng of cyclosporin A/g of cornea persists for 24 hours in the cornea. In the cornea, the 24-hour nycthemeral immunomodulator cover is therefore satisfactory.

Moreover, no passage into the aqueous humor was observed and passage into the blood was insignificant.

In conclusion, the efficacy of the solution according to the invention has been demonstrated since the values obtained are of the same order as the partial data available for RESTASIS™ (ophthalmic emulsion containing cyclosporine (0.05%), glycerin, castor oil, polysorbate 80, carbomer copolymer type A, purified water, and sodium hydroxide) and are compatible with those in the literature which recommends a concentration of active substance in the target tissues of 100 to 400 ng/g to obtain an immunomodulatory effect.

The invention claimed is:

1. An aqueous ophthalmic solution comprising an immunosuppressive agent, a first polymer, a second polymer, and a third polymer, wherein:
    the immunosuppressive agent is cyclosporin A, wherein cyclosporin A is equal to or greater than 0.05% by weight of the solution;
    the first polymer is a cellulose derivative;
    the second polymer is a polyvinyl derivative; and
    the third polymer is a polymer with a lipophilic functional group.
2. The solution according to claim 1, wherein cyclosporin A is between 0.05 and 0.1% by weight of the solution.
3. The solution according to claim 1, wherein the solution does not contain an antimicrobial preservative.

4. The solution according to claim 3, wherein the solution does not contain any quaternary ammonium antimicrobial preservative.

5. The solution according to claim 4, wherein the solution does not contain benzalkonium chloride (BAK).

6. The solution according to claim 1, wherein the Brookfield viscosity of the solution at 25° C. is below 50 mPa·s.

7. The solution according to claim 1, wherein the Brookfield viscosity of the solution at 25° C. is between 5 and 15 mPa·s.

8. The solution according to claim 1, wherein the cellulose derivative is a cellulose ether.

9. The solution according to claim 1, wherein the cellulose derivative is selected from the group consisting of methylcellulose, ethylcellulose, hydroxyethylcellulose, hydroxypropylcellulose, carboxymethylcellulose, hydroxypropylmethylcellulose, and salts thereof.

10. The solution according to claim 1, wherein the cellulose derivative is sodium carboxymethylcellulose.

11. The solution according to claim 1, wherein the polyvinyl derivative is a polyvinyl alcohol derivative.

12. The solution according to claim 1, wherein the polymer with a lipophilic functional group is a macrogolglycerol hydroxystearate.

13. The solution according to claim 1, wherein the polymer with a lipophilic functional group is macrogolglycerol hydroxystearate 40.

14. The solution according to claim 1, wherein the first polymer is between 0.1 and 3% by weight of the solution.

15. The solution according to claim 1, wherein the first polymer is between 0.5 and 1.5% by weight of the solution.

16. The solution according to claim 1, wherein the first polymer is 0.8% by weight of the solution.

17. The solution according to claim 1, wherein the second polymer is between 0.25 and 3% by weight of the solution.

18. The solution according to claim 1, wherein the second polymer is 0.5% by weight of the solution.

19. The solution according to claim 1, wherein the third polymer is between 0.5 and 20% by weight of the solution.

20. The solution according to claim 1, wherein the third polymer is between 5 and 15% by weight of the solution.

21. The solution according to claim 1, wherein the third polymer is 10% by weight of the solution.

22. A method for treating a disorder of the surface of the eye which has an inflammatory or immunological basis comprising administering a solution according to claim 1 to the eye of a subject.

23. The method of claim 22, wherein the disorder is dry eye syndrome or loss of corneal sensitivity.

24. The method of claim 22, wherein the step of administering comprises administering one or more drops per day of the solution topically into each eye of the subject.

25. A method for preparing a solution according to claim 1 comprising the steps of:
   solubilising the immunosuppressive agent in the presence of at least a fraction of the first polymer in the presence of water;
   mixing any remaining fraction of the first polymer with the second and third polymers, water, and optionally a buffer system and isotonifying agent; and
   mixing the products obtained in the previous steps.

26. The solution according to claim 1, wherein the polyvinyl derivative is polyvinyl alcohol.

27. The solution according to claim 1, wherein cyclosporin A is equal to or greater than approximately 0.1% by weight of the solution.

28. The solution according to claim 1 or 27, wherein cyclosporin A is lower than or equal to approximately 0.2% by weight of the solution.

* * * * *